US 7,850,682 B2

United States Patent
Amir et al.

(12) United States Patent
(10) Patent No.: US 7,850,682 B2
(45) Date of Patent: Dec. 14, 2010

(54) SYSTEMS FOR MRI-GUIDED CRYOSURGERY

(75) Inventors: Uri Amir, Yehuda (IL); Nir Berzak, Zikhron-Yaakov (IL); Mordechai Bliweis, Haifa (IL); Yura Leybin, Haifa (IL); Ron Hillely, Zichron Yaakov (IL)

(73) Assignee: Galil Medical Ltd., Yokneam (IL)

( * ) Notice: Subject to any disclaimer, the term of this patent is extended or adjusted under 35 U.S.C. 154(b) by 873 days.

(21) Appl. No.: 11/030,887

(22) Filed: Jan. 10, 2005

(65) Prior Publication Data
US 2006/0155268 A1     Jul. 13, 2006

(51) Int. Cl.
*A61B 18/02* (2006.01)
(52) U.S. Cl. ............................................ 606/21; 606/22
(58) Field of Classification Search .............. 606/20–26; 600/411, 412, 417
See application file for complete search history.

(56) References Cited

U.S. PATENT DOCUMENTS

| | | | |
|---|---|---|---|
| 5,433,717 A * | 7/1995 | Rubinsky et al. ............... 606/20 |
| 5,522,870 A | 6/1996 | Ben-Zion |
| 5,540,062 A | 7/1996 | Maytal |
| 5,603,221 A | 2/1997 | Maytal |
| 5,706,810 A | 1/1998 | Rubinsky et al. |
| 5,978,697 A * | 11/1999 | Maytal et al. ................ 600/411 |
| 6,235,018 B1 * | 5/2001 | LePivert ...................... 606/20 |
| 6,496,007 B1 | 12/2002 | Damadian et al. |
| 6,575,969 B1 | 6/2003 | Rittman, III et al. |
| 6,584,360 B2 * | 6/2003 | Francischelli et al. ......... 607/98 |
| 6,694,170 B1 | 2/2004 | Mikus et al. |
| 6,704,592 B1 * | 3/2004 | Reynolds et al. ............ 600/411 |
| 7,048,732 B2 * | 5/2006 | Ellingsen ..................... 606/20 |
| 7,101,367 B2 | 9/2006 | Xiao et al. |
| 7,294,127 B2 * | 11/2007 | Leung et al. .................. 606/41 |
| 7,344,530 B2 | 3/2008 | Bischof et al. |
| 7,402,161 B2 * | 7/2008 | Zvuloni et al. ................ 606/20 |

(Continued)

FOREIGN PATENT DOCUMENTS

WO    WO 2006/072958    7/2006

OTHER PUBLICATIONS

Official Action Dated Dec. 5, 2007 From the US Patent Office Re.: U.S. Appl. No. 11/030,887.

(Continued)

*Primary Examiner*—Michael Peffley
(74) *Attorney, Agent, or Firm*—Fredrikson & Byron, P.A.

(57) ABSTRACT

The present invention is of systems and methods for MRI-guided cryosurgery. The systems enable a surgeon positioned next to a patient and within an MRI magnetic environment both to monitor progress of a cryosurgical intervention by observing MRI images of the intervention in real time, and to fully control aspects of operation of a cryosurgery apparatus by remotely controlling a fluid supply source positioned external to that magnetic environment, which fluid supply source supplies cryogenic fluids to cryoprobes operable within that magnetic environment, thereby enabling real-time MRI-guided control of a cryoablation process. A preferred embodiment enables calculation and display of borders of an ablation volume surrounding a cooled cryoprobe in real time, and further enables automatic control of elements of a cryoablation procedure, which elements are triggered when shape and position of that calculated ablation volume are found to bear a predefined relationship to the shape and position of a predefined treatment target.

54 Claims, 6 Drawing Sheets

U.S. PATENT DOCUMENTS

2006/0155267 A1   7/2006   Berzak et al.
2006/0155268 A1   7/2006   Amir et al.

OTHER PUBLICATIONS

Official Action Dated Sep. 12, 2008 From the US Patent Office Re.: U.S. Appl. No. 11/030,887.
IPRP CH I.
Official Action Dated Apr. 27, 2009 From the US Patent and Trademark Office Re.: U.S. Appl. No. 11/106,438.
Official Action Dated Dec. 7, 2009 From the US Patent and Trademark Office Re.: U.S. Appl. No. 11/106,438.
International Search Report Dated Jul. 28, 2006 From the International Searching Authority Re.: Application No. PCT/IL2006/00028.
Written Opinion Dated Jul. 28, 2006 From the International Searching Authority Re.: Application No. PCT/IL2006/000028.

* cited by examiner

SYSTEMS FOR MRI-GUIDED CRYOSURGERY

FIELD AND BACKGROUND OF THE INVENTION

The present invention relates to devices, systems, and methods for MRI-guided cryosurgery. More particularly, the present invention relates to a cryosurgery apparatus compatible for use within the magnetic environment of a functioning magnetic resonance imaging system and fully controllable by a surgeon positioned within that magnetic environment, wherein the cryosurgery apparatus is also optionally operable under algorithmic control, control decisions being based on information gleaned from MRI monitoring of a cryosurgery procedure in real time.

The present application relates to the use of cryosurgical tools in an MRI environment.

In the early days of magnetic resonance imaging, MRI was used only as a diagnostic tool. MRI imaging was used to visualize body tissues and to locate and evaluate problematic tissue structures. When MRI-assisted diagnosis identified problems correctable by non-invasive surgery, non-MRI imaging modalities (ultrasound, x-ray and fluoroscopy endoscopic and laparoscopic cameras, etc.) were typically used to monitor the surgical procedure in real time. More recently techniques have been developed to use MRI during surgery. Use of MRI in real time has major advantages for certain kinds of surgery, yet presents unique problems relating to the compatibility of equipment used within MRI's powerful magnetic environment. Use of magnetic resonance imaging presents particular advantages for monitoring of cryosurgery procedures, yet existing systems for MRI-compatible cryosurgery have significant limitations and disadvantages.

Cryoablation of tissues has become an increasingly popular method of treatment for a variety of pathological conditions. Malignancies in body organs such as the breast, prostate, kidney, liver, and other organs are successfully treated by cryoablation, and a variety of non-malignant pathological conditions, such as benign prostate hyperplasia, benign breast tumors, and similar growths are also well treated by cryoablation of unwanted tissues. Certain cases of intractable chronic pain ate also treatable through cryosurgery, by cryoablation of selected nervous tissue.

Cryoablation of pathological tissues or other unwanted tissues is most often accomplished by utilizing standard medical imaging modalities to identify and locate a locus for ablative treatment. Once a treatment locus has been identified and located, one or more cryoprobes are inserted into the selected locus, then cooled sufficiently to cause the tissues surrounding the treatment heads to reach cryoablation temperatures. Depending on the treatment protocol, tissues may be thawed and refrozen. Tissues thus treated loose their functional and structural integrity. Cancerous cells cease growing and multiplying, and cryoablated tumor tissue materials, whether from malignant tumors or from benign growths, lose their structural integrity and are subsequently sloughed off or absorbed by the body.

Cryoablation temperatures are temperatures at which cellular structure and functionality of tissues are reliably destroyed. In current practice cryoablation temperatures are generally taken to be in the approximate range of $-40°$ C. and below, though of course final determination of appropriate cryoablation temperature is the responsibility of the surgeon in view of the particular circumstances of each clinical case.

When a cryoprobe is cooled to cryoablation temperatures, a volume of frozen tissue forms around the probe, commonly called an "iceball". A cryoablation iceball contains a first volume of tissue, sometimes referred to herein as an "ablation volume", which ablation volume is adjacent to the probe and cooled to cryoablation temperatures. The first (ablation) volume is surrounded by a second volume of tissue cooled to temperatures above cryoablation temperature but below the freezing point of water. Within the ablation volume cellular structure and function are reliably destroyed. Within the second volume, tissues are damaged to varying degrees, yet their structure and function are not reliably destroyed.

It is a major limitation of existing imaging modalities that they are unable to display to a surgeon the border separating those first and second volumes.

Arriving at a correct understanding of the position and three-dimensional shape of that border is of critical importance to a surgeon performing a cryoablation. If he underestimates the extent of the ablation volume, he destroys healthy tissue unnecessarily. If he overestimates the extent of the ablation volume, he risks failing to destroy dangerous functional pathological (e.g. malignant) tissue structures.

Lack of systems providing accurate information on the size and position of an actual cryoablation volume is a major unsolved problem of contemporary cryoablation technique.

Currently known non-MRI imaging modalities are not adjusted nor designed to directly image the size and position of an actual cryoablation volume. MRI imaging is capable of detecting and displaying tissue temperatures, yet no MRI system commercially available today is able to detect and display the borders of a cryoablation volume, because available MRI systems cannot detect and display temperatures within frozen tissue. Although MRI detection of temperatures within very cold temperature ranges appears to be theoretically possible, no MRI system commercially available today provides this capability.

Given the limitations of currently available techniques as described above, cryosurgeons are forced to estimate the position and size of the first (ablation) volume, based on available information, and in particular based on detected size and position of the second (frozen tissue) volume.

X-ray technologies, such as fluoroscopy, are capable of showing the borders of a frozen volume (the "iceball"), yet they show only a projected shadow of the iceball perpendicular to the main axis of the x-rays. Ultrasound clearly shows an external iceball border, but shows only the iceball border that is closest to the ultrasound probe. (That is, ultrasound shows only the portion of the border between frozen and non-frozen tissue which is situated between the frozen tissue and the ultrasound probe.) The opposite border is not visible in the ultrasound display. A plurality of synchronized ultrasound probes directed towards the iceball from various surrounding positions would provide better information, but such a solution has been found to be impractical in some cases and impossible in other cases. Thus, both ultrasound and x-ray technologies deliver only partial information concerning the size and position and three-dimensional shape of the iceball, and neither can deliver direct information concerning the size and position and three-dimensional shape of the cryoablation volume contained within the iceball boundaries.

For the purpose of understanding the size and position of an ablation volume, information provided by magnetic resonance imaging is superior to that available from x-ray and ultrasound imaging methods.

In the future, MRI systems may provide capability of direct imaging of an isotherm within frozen tissue, such as for example, the $-40°$ C. isotherm which, according to current clinical thinking, marks the external border of the ablation volume.

Currently available MRI systems provide three other types of information which may be used to achieve accurate estimations of the position of that border.

First, a plurality of MRI 'slices' showing the border of frozen tissue, the external border of the iceball, permit to visualize the entire shape of the iceball as a whole and in detail, independent of any particular direction or point of view. Using known techniques, a plurality of such 'slices' may be combined algorithmically to create a solid model of the iceball in three dimensional space.

Second, MRI's ability to measure temperatures in non-frozen tissues permits to develop an appreciation of thermal gradients within tissues surrounding the iceball.

Third, MRI images can provide accurate information relating to the exact position of an operating cryoprobe within treated tissue. This information, together with temperature data available from sensors within the probe itself can contribute to estimation of temperature distribution within the frozen tissues.

These three abilities provide raw materials for accurate estimations of the size and position of an ablation volume concealed within a detectable iceball. Accurate estimation of the size and position of an ablation volume is critically important in cryosurgery, since it is generally a goal of cryosurgery to ablate all pathological tissue while destroying and damaging as little as possible of healthy tissue surrounding the pathological tissue. It is thus critically important that a surgeon, during a procedure, have a good and accurate understanding of what tissues he has frozen, and what tissues he has reliably killed. A surgeon who is unable to observe or accurately estimate the size and shape of an ablation volume is forced systematically underestimate the size of the ablation volume, at least when dealing with malignant or possibly malignant tumors, because total destruction of the entire tumor is essential to treatment, lest potentially lethal live cancer cells be left behind following surgery. A cryosurgeon lacking accurate means for observing or estimating the position of the borders of an ablation volume is forced to err on the side of caution, and to extend cryoablation well beyond the locus where ablation is actually needed and desired. He thereby avoids uncertainty about whether all portions of a lesion (e.g., a malignant tumor) have been reliably destroyed, but unfortunately destroys considerable healthy tissue along with the lesion whose ablation is desired.

Thus it is to be expected that a system rendering visible the border of an ablation volume, or alternatively a system facilitating accurate estimation of the size and position of such a border, would reduce hospital stays, decrease danger of surgical complications, speed recovery, and avoid various deleterious consequences to the long-term health and quality of life of the recovering patient.

For this and other reasons, practice of cryosurgery under real time MRI monitoring is highly desirable.

However, practice of cryosurgery under real-time MRI monitoring is difficult to accomplish. Several obstacles must be overcome.

The cryosurgical equipment must be such as to be substantially unaffected by the MRI system's powerful magnetic field. A cryoprobe constructed of non-MRI-compatible materials may be subjected to powerful undesired forces generated by magnetic interaction between the probe and the MRI magnetic field, and/or may distort the magnetic field and thereby create distortion of the MRI image. It has been found that cryoprobes and associated hardware constructed from materials such as titanium and inconel are not subjected to strong forces induced by magnetic fields of imaging equipment, and do not distort MRI images.

Electrical circuits used within the MRI environment must be shielded, lest they be subject to undesired induced currents generated within the electrical circuitry. Induced currents can lead to uncontrolled phenomena such as distorted data and/or distorted control signals.

Cryosurgery equipment for use within an MRI environment must also be such as not to cause distortion of the MRI's sensitive image-generating processes. Electric currents induced by an external magnetic field interacting with components of electronic circuitry could have such a distorting effect, as could electromagnetic radiation generated by the electrical circuitry during its normal operation. In particular, electronic circuits with switching components switching at high frequencies (e.g., computers) and with potential for broadcasting (intentionally or otherwise) electromagnetic fields generated thereby, must be shielded. Several layers of μ-metal (mu-metal) have been found to successfully isolate electronic circuits from MRI antenna.

Thus, cryosurgery equipment usable within an MRI environment must be made of MRI-compatible material, and electronic circuitry included in the cryosurgery equipment, if any, must be shielded by several layers of μ-metal or the equivalent. Preferably, MRI-compatible cryosurgery equipment should be as convenient, safe, and effective as 'normal' (non MRI compatible) cryosurgery equipment.

U.S. Pat. No. 5,978,697 to Maytal presents elements of an MRI-compatible cryosurgery system, and is here included by reference Maytal's system provides two modules and a set of connecting links between them.

A first module, referred to herein as an "inside" module, is for use inside an MRI "room" (that is, inside an MRI magnetic environment), and includes Joule-Thomson cryoprobes insertable in a patient during a cryosurgical intervention, which cryoprobes are operable to cool to cryoablation temperatures when supplied with high-pressure cooling gas, and further operable to heat, for disengagement from adhering frozen tissues, when supplied with high-pressure heating gas. The cryoprobes comprise simple control elements such as buttons operable by a surgeon, for passing from one phase of operation (e.g., cooling) to another phase of operation, (e.g., heating).

A second module, referred to herein as an "outside" module, is for use outside an MRI magnetic environment and is positioned away from the immediate environment of the operating surgeon. The outside module provides a support infrastructure for op cryoprobe and other equipment of the inside module.

The outside module stands outside the magnetic environment of the MRI system, and, is typically distanced from the immediate vicinity of the patient. The outside module includes a gas supply for supplying high pressure heating gas and high-pressure cooling gas, and has various manual and automatic valves for controlling gas flow. The outside module also has a user interface operable to display operating status of the cryoprobes and other equipment of the inside module, and is, further operable to accept commands from an operator. An operator interacting with the outside module can view information received, analyzed, and displayed by the outside module, which information is at least partially based on data from sensors within the inside module.

The operator interacting with the outside module can control operation of the outside module, and thereby (e.g., by controlling valves of the outside module which govern flow of high-pressure gasses to the inside module) thereby control functions of the inside module as well.

In the system taught by Maytal, inside module and outside module are linked by, gas supply lines and by electronic data transmission lines. Maytal teaches methods and configurations for providing such lines linking an inside and outside modules, including the method of providing a channel within the MRI magnet itself to accommodate gas and data lines linking inside and outside modules.

A major disadvantage of the configuration taught by Maytal is the described separation of control functions into inner and outer modules, which configuration provides user access to some control functions from within the inner module (e.g., control buttons selecting cooling or heating of cryoprobes), yet provides user access to other control functions from the outer module (e.g., manual control of gas valves, user interface for viewing a display reporting cryosurgery system status, etc.) In practice, systems conforming to the teachings of Maytal required two operators of the cryosurgical equipment, a first operator being a surge on, positioned within the magnetic field of the MRI equipment within an operating theatre environment, which first operator manipulates cryoprobes to perform the cryoablation, and a second operator who interacts with the user interface of the outer module, whose function includes inputting gas control commands and reporting orally to the surgeon, providing ongoing reports on cryosurgery system status which the surgeon, from his position near the patient, cannot see for himself and cannot directly control.

Maytal's system thus suffers from a serious disadvantage of inconvenience, in that it requires two operators, physically separated from one another, to operate the system, and in that the surgeon, in contact with a patient during the cryoablation does not have direct control over a variety of aspects of the cryoablation procedure. Maytal's system is further disadvantageous in that the separation of functions into two modules as described does not allow for combined or coordinated presentation of both of cryosurgery status data and of MRI imaging data within a common display interface.

Thus, there is a widely recognized need for, and it would be highly advantageous to have, an MRI-compatible cryosurgery system operable to provide direct control of cryosurgery components by an operating surgeon positioned within or near an MRI magnetic environment in a position convenient for operating on a patient, the system enabling real-time MRI monitoring of an on-going cryosurgery procedure.

There is further a widely recognized need for, and it would be highly advantageous to have, an apparatus for MRI-guided cryosurgery wherein display and control functions of the cryosurgery apparatus are integrated with display and control functions of the MRI apparatus, in a common display and with ergonomically compatible sets of controls for the two apparatus.

As stated above, currently available MRI systems do not provide direct information relating to size, position, and three-dimensional shape of the volume of total destruction (the ablation volume) created within an iceball during a cryoablation process. Yet such information would be of great use to a surgeon during a cryoablation procedure. Current MRI systems do not make recommendations to a surgeon during a cryoablation procedure, nor provide analyses specific to cryosurgical needs, nor do they automatically or partially automatically control the cryoablation procedure. Thus, there is a widely recognized need for, and it would be highly advantageous to have a cryosurgery system providing real-time recommendations to a surgeon during a cryosurgery procedure, and providing automatic or semi-automatic control of cryoablation equipment used in the body of a patient, based on algorithmic analyses of detected tissue configurations and of detected tissue temperature information gleaned from MRI image analysis.

SUMMARY OF THE INVENTION

According to one aspect of the present invention there is provided an MRI-compatible cryosurgery system usable to perform cryoablation of tissues in a body of a patient, comprising (a) an MRI-compatible intervention module which comprises at least one MRI-compatible cryoprobe, which cryoprobe is operable to be inserted into the body of a patient and to cryoablate tissues therein; (b) an MRI-compatible-cryosurgery control module which comprises a shielded electrical circuit, which control module is operable to send commands to a cryosurgery support module; (c) a cryosurgery support module which comprises a supply of a coolant fluid, which support module is operable to deliver the coolant fluid to a fluid supply conduit in response to a command received from the control module; and (d) a fluid supply conduit operable to deliver a coolant fluid from the support module to the cryoprobe, wherein at east a portion of the supply conduit adjacent to the cryoprobes constructed of MRI-compatible material.

According to further features in preferred embodiments of the invention described below, the cyroprobe is operable to be cooled by expansion of high-pressure cooling gas through a Joule-Thomson orifice, or is operable to be cooled by evaporation of the coolant fluid. Preferably, the cryoprobe is selectively operable to be heated and to be cooled, and may be coolable by expansion of high-pressure heating gas through a Joule-Thomson orifice. The intervention module preferably comprises a plurality of cryoprobes, and may also comprise an MRI-compatible template operable to guide insertion of the cryoprobe into the body of the patient, an electromechanical device operable to move the cryoprobe within the body of the patient, an MRI-compatible guide wire operable to be positioned within the body of the patient, and operable to guide positioning of the cryoprobe within the body of the patient, and a thermal sensor operable to be positioned at a selected position with the body of the patient and to report temperature of the body at the selected position. The cryoprobe may comprise a thermal sensor operable to report temperatures within the cryoprobe or to, report temperature external to the cryoprobe. The cryoprobe is at least partially constructed of MRI-compatible material, and is preferably entirely constructed of MRI-compatible material. The cryoprobe may preferably be constructed of titanium or of inconel.

According to further features in preferred embodiments of the invention, described below the cryosurgery control module comprises an interface for receiving operational commands from an operator. The cryosurgery control module is constructed of MRI-compatible materials and is operable to send commands to the cryosurgery support module while positioned in proximity to a surgeon and within, an MRI environment. Preferably the cryosurgery control module is operable to receive and interpret oral commands from a human operator, and may be operable to be positioned external to an MRI environment and to receive and interpret oral commands from a human operator positioned within the MRI environment. The system preferably also comprises a display operable to display information pertaining to operational status of the cryoprobe, to display information gleaned from sensors positioned within the body of the patient, and to display information pertaining to operational status of the cryosurgery support module. The display is preferably MRI-compatible.

According to further features in preferred embodiments of the invention described below, the cryosurgery support module comprises a source of high-pressure cooling gas and a source of high-pressure heating gas, and the cryosurgery support module is operable to selectively deliver to the fluid conduit a gas selected from a group consisting of a high-pressure heating gas and a high-pressure cooling gas.

According to another aspect of the present invention there is provided a system for MRI-guided cryosurgery, comprising (a) an MRI-compatible cryosurgery apparatus usable to perform cryoablation of tissues in a body of a patient, which comprises (i) an MRI-compatible intervention module which comprises at least one MRI-compatible cryoprobe, which cryoprobe is operable to be inserted into the body of a patient and to cryoablate tissues therein; (ii) an MRI-compatible cryosurgery control module which comprises a shielded electrical circuit, which control module is operable to send commands to a cryosurgery support module; and (iii) a cryosurgery support module which comprises a supply of coolant fluid, which support module is operable to deliver the coolant fluid to a fluid supply conduit in response to a command received from the control module; and (iv) a fluid supply conduit operable to deliver a coolant fluid from the support module to the cryoprobe, wherein at least a portion of the supply conduit adjacent to the cryoprobe is constructed of MRI-compatible materials; and (b) an MRI apparatus operable to generate and to display magnetic resonance images of a patient during a cryosurgery procedure, the MRI imaging apparatus comprises (i) an MRI command module operable to receive MRI operating commands from an operator and to modify MRI imaging performed by the MRI imaging apparatus according to the MRI operating commands; and (ii) an MRI display module operable to display to an operator images of a portion of a body of a patient, the images being generated by the MRI apparatus.

According to further features in preferred embodiments of the invention described below, the cryosurgery control module comprises an interface for receiving operational commands from, an operator. The cryosurgery control module is constructed of MRI-compatible materials and is operable to send commands to the cryosurgery support module while positioned in proximity to a surgeon and within an MRI environment, and is operable to receive and interpret oral commands from a human operator. The control module preferably comprises a cryosurgery display operable to display operational status of elements of the cryosurgery apparatus. Preferably the MRI command module and the cryosurgery command module are a common integrated command module, and the MRI display module and the cryosurgery display are a common integrated display.

According to further features in preferred embodiments of the invention described below, the system further comprises a temperature observation module operable to detected body temperature information from frozen tissue.

According to still further features in preferred embodiments of the invention described below, the system further comprises a temperature estimation module operable to estimate position of an isotherm at a pre-determined temperature within the body of a patient, based on detected position of at least one cryoprobe and detected position of an iceball border. Preferably, the MRI display is operable to display the estimated isotherm.

According to yet further features in preferred embodiments of the invention described below, the system comprises an analytical module operable to calculate a position in three-dimensional space of a border of an ablation volume formed around a functioning cryoprobe within a body of a patient. The calculation may be based on data gleaned from analysis of a plurality of MRI images, at least one of the MRI images showing a position of the cryoprobe prior to cooling of the cryoprobe, and at least one of the MRI images showing a position of a border of frozen tissue surrounding the cryoprobe during cooling of the probe.

According to further features in preferred embodiments of the invention described below, there is provided a calculation module operable to calculate a position in three-dimensional space of a border of a volume of tissue reliably cooled to a predetermined temperature, the calculation being based on tissue temperature information gleaned from analysis of data provided by the MRI module. Preferably, the cryosurgery control module is further operable to generate a command to the cryosurgery support system, which command is based on an algorithmic response to the calculated position of the ablation volume. The generated command may be operable to control cooling of the cryoprobe, or to control heating of the cryoprobe. Additionally, the system may further comprise an electromechanical device for moving the cryoprobe within the body of the patient, and the generated command may be operable to control positioning of the cryoprobe by the electromechanical device.

According to yet another aspect of the present invention there is provided an MRI-guided cryosurgery apparatus for performing MRI-guided cryosurgery in the body of a patient, comprising (a) an MRI-compatible cryoablation system; (b) a magnetic resonance imaging system; and (c) a control module operable to issue an operative command to the cryoablation system when an algorithmic process determines, by examination of data gleaned from the MRI system, that a trigger condition exists in the body of the patient.

The trigger condition may be detection of an isotherm in the body at a predetermined position within the body, or detection of cooling to a predetermined degree at a predetermined locus within the body, or be a calculated determination that a calculated ablation volume border includes all of a predefined treatment target volume within the body of the patient. The trigger condition may be determined by, comparing an estimated position of a first isotherm within a body with a predefined three-dimensional shape, and wherein estimation of the estimated position of the first isotherm is determined by calculation based on a detected position of a second isotherm detected within the body, where the second isotherm may be a detect ed border of an iceball within the body.

According to still another aspect of the present invention there is provided a method for guiding guided cryosurgery by calculating an estimated border of as cryoablation volume within the body of a patient based on data provided by magnetic resonance imaging of the body, comprising (a) recording a position of a cryoprobe within tissues of the body prior to creating an iceball surrounding the probe; (b) cooling the probe to form an iceball surrounding the probe, and recording position of a three-dimensional borders of the iceball; (c) selecting a distance ratio usable to determine status of subunits of tissue within the iceball; (d) digitally subdividing tissue within the iceball into subunits; (e) determining for each subunit whether it is within an ablation volume by calculating a first distance of the each subunit from a nearest cooling portion of the cryoprobe and a second distance of the each subunit from a nearest border of the iceball, and determining that the subunit is within the ablation volume if the first distance divided by a sum of the first and second distances is less than the selected distance ratio, and determining that the subunit is outside the ablation volume if the first distance divided by a sum of the first and second distances is greater than the selected distance ratio.

According to further features in preferred embodiments of the invention described below, the method further comprises displaying an image of at least a portion of the estimated cryoablation volume border, or comparing the estimated cryoablation volume border to a predetermined cryoablation target to determine whether the predetermined cryoablation target is contained within the cryoablation volume. Preferably, the method further comprises issuing notification to a surgeon if the cryoablation target is determined to be contained within the cryoablation volume, or issuing a command to a cryoablation apparatus if the cryoablation target is determined to be contained within the cryoablation volume.

The present invention successfully addresses the shortcomings of the presently known configurations by providing an MRI-compatible cryosurgery system operable to provide direct control of cryosurgery components by an operating surgeon positioned within or near an MRI magnetic environment in a position convenient for operating on a patient, the system enabling real-time MRI monitoring of an on-going cryosurgery procedure.

The present invention further successfully addresses the shortcomings of the presently known configurations by providing an apparatus for MRI-guided cryosurgery wherein display and control functions of the cryosurgery apparatus are integrated with display and control functions of the MRI apparatus, in a common display and with ergonomically compatible sets of controls for the two apparatus.

The present invention further successfully addresses the shortcomings of the presently known configurations by providing a cryosurgery system providing real-time recommendations to a surgeon during a cryosurgery procedure, and providing automatic or semi-automatic control of cryoablation equipment used in the body of a patient, based on algorithmic analyses of detected tissue configurations and of detected tissue temperature information gleaned from MRI image analysis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
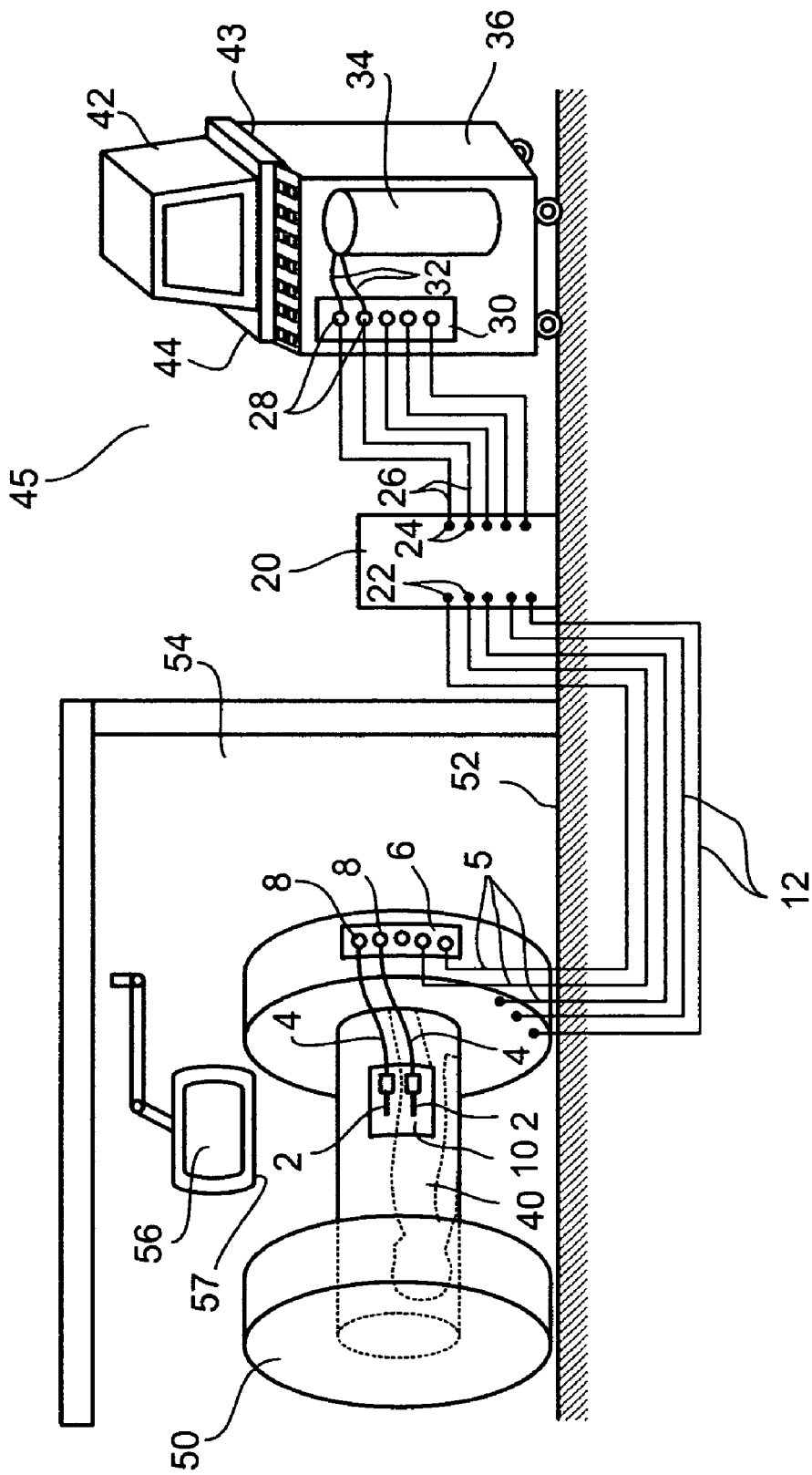
FIG. 1 is a simplified schematic of an MRI-compatible cryoprobe system, according to methods of prior art.

The present invention is of systems and methods for MRI-guided cryosurgery. Specifically, the present invention enables a surgeon positioned next to a patient and within an MRI magnetic environment both to monitor progress of a cryosurgical intervention by observing MRI images of the intervention in real time, and to fully control aspects of operation of a cryosurgery apparatus by remotely controlling a fluid supply source positioned external to that magnetic environment, which fluid supply source supplies cryogenic fluids to cryoprobes operable within that magnetic environment, thereby enabling real-time MRI-guided control of a cryoablation process. A preferred embodiment enables calculation and display of borders of an ablation volume surrounding a cooled cryoprobe in real time, and further enables automatic control of elements of a cryoablation procedure, which elements are triggered when shape and position of that calculated ablation volume are found to bear a predefined relationship to the shape and position of a predefined treatment target.

Before explaining at least; one embodiment of the invention in detail, it is to be understood that the invention is not, limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

To enhance clarity of the following descriptions, the following terms and phrases will first be defined.

The phrase "heat-exchanging configuration" is used herein to refer to component configurations traditionally known as "heat exchangers", namely configurations of components situated in such a manner as to facilitate the passage of heat from one component to another. Examples of "heat-exchanging configurations" of components include a porous matrix used to facilitate heat exchange between components, a structure integrating a tunnel within a porous matrix, a structure including a coiled conduit within a porous matrix, a structure including a first conduit coiled around a second conduit, a structure including one conduit within another conduit, or any similar structure.

The phrase "Joule-Thomson heat exchanger" as used herein refers, in general, to any device used for cryogenic cooling or for heating, in which a gas is passed from a first region of the device, wherein it is held under higher pressure, to a second region of the device, wherein it is enabled to expand to lower pressure. A Joule-Thomson heat exchanger may be a simple conduit, or it may include an orifice, referred to herein as a "Joule-Thomson orifice", through which gas passes from the first, higher pressure, region of the device to the second, lower pressure, region of the device. A Joule-Thomson heat exchanger may further include a heat-exchanging configuration, for example a heat-exchanging configuration used to cool gasses within a first region of the device, prior to their expansion into a second region of the device.

The phrase "cooling gasses" is used herein to refer to gasses which have the property of becoming colder when passed through a Joule-Thomson heat exchanger. As is well known in the art, when gasses such as argon, nitrogen, air, krypton, $CO_2$, $CF_4$ and xenon, and various other gasses pass from a region of high pressure to a region of lower pressure in a Joule-Thomson heat exchanger, these gasses cool and may to some extent liquefy, creating a cryogenic pool of liquefied gas. This process cools the Joule-Thomson heat exchanger itself, and also cools any thermally conductive materials in contact therewith. A gas having the property of becoming colder when passing through a Joule-Thomson heat exchanger is referred to as a "cooling gas" in the following.

The phrase "heating gasses" is used herein to refer to gasses which have the property of becoming hotter when passed through a Joule-Thomson heat exchanger. Helium is an example of a gas having this property. When helium passes from a region of higher pressure to a region of lower pressure, it is heated as a result. Thus, passing helium through a Joule-Thomson heat exchanger has the effect of causing the helium to heat, thereby heating the Joule-Thomson heat exchanger itself and also heating any thermally conductive materials in contact therewith. Helium and other gasses having this property are referred to as "heating gasses" in the following.

As used herein, a "Joule Thomson" cooler is a Joule Thomson heat exchanger used for cooling. As used herein, a "Joule Thomson heater" is a Joule Thomson heat exchanger used for heating.

The term "ablation temperature", as used herein, is the temperature at which cell functionality and structure are destroyed by cooling. Temperatures below approximately −40° C. are generally considered to be ablation temperatures.

The term "ablation volume", as used herein, is, the volume of tissue which has been cooled to ablation temperatures by one or more cryoprobes.

As used herein, the term "high-pressure" as applied to a gas is used to refer to gas pressures appropriate for Joule-Thomson cooling of cryoprobes. In the case of argon gas, for example, "high-pressure" argon is typically between 3000 psi and 4500 psi, though somewhat higher and lower pressures may sometimes be used.

It is expected that during the life of this patent many relevant cryoprobes will be developed, and the scope of the term "cryoprobe" is intended to include all such new technologies a priori.

Similarly, it is expected that during the life of this patent many relevant techniques for magnetic resonance imaging will be developed, and the scopes of the terms "MRI" and "magnetic resonance imaging" are intended to include all such new technologies a prior.

The term "MRI" is used herein as an abbreviation for "magnetic resonance imaging". The terms "MRI" and "magnetic resonance imaging" are used interchangeably in the following. The terms "MRI magnetic environment" and "MRI environment" are used to refer to the powerful magnetic field created by MRI magnets which are a component of MRI systems. The MRI magnetic environment typically contains all or part of a patient's body when that body undergoes MRI imaging.

As used herein the term "about" refers to ±10%.

In discussion of the various figures described hereinbelow, like numbers refer to like parts.

Figure 2:
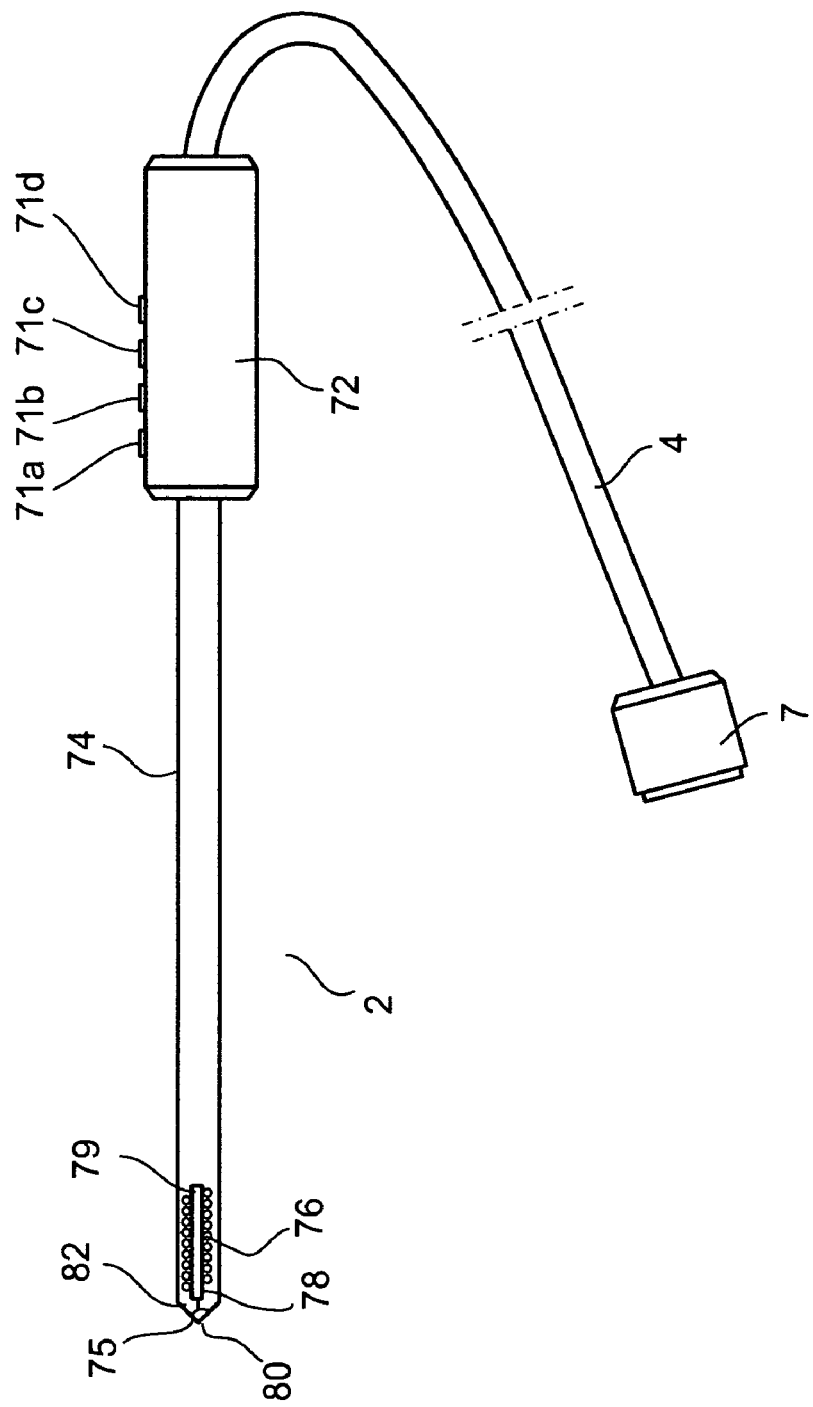
FIG. 2 is a simplified schematic of a cryosurgery device according to methods of prior art.

For purposes of better understanding the present invention, as illustrated in FIGS. 3-7 of the drawings, reference is first made to the construction and operation of is conventional (i.e., prior) MRI-compatible cryoprobe system as illustrated in FIGS. 1-2.

Attention is now drawn to FIG. 1, which presents a simplified schematic of an MRI-compatible cryoprobe system, according to methods of prior art.

FIG. 1 includes an "open" MRI magnet 50, for accommodating a patient 40, the MRI magnet including at least one aperture 10 for allowing access of a surgeon to the patient. Magnet 50 includes at least one channel so as to enable installation of electrical and/or mechanical connecting lines such as gas tubes generally denoted as within the MRI magnet. As shown in the figure, connecting lines 5 terminate at surgical tools thereto.

As shown in the figure, a plurality of cryosurgery operating members 2 for operating a patient are connected to connection sites 8, the operating members being remotely controlled by a remote control unit 45 located externally to MRI room 54. Each of operating members 2 preferably includes a Joule-Thompson heat exchanger for effectively cooling the operating member.

An underground passageway including underground connecting lines 12 connectable to lines 5 extends from MRI magnet 50 to control unit 15 located externally to MRI room 54. As, shown in the figure connection lines 12 are preferably connected to an immobilized linking box 20 located externally to MRI room 54 via a first set of connection sites 22.

Thus, linking box 20 includes a first set of connection sites 22 for receiving a set of connecting lines 12, and a second et of connection sites 24 for receiving a set of gas tubes 26 arriving from the control unit 45 of the cryosurgery device. Gas tubes 26 are preferably flexible and detachably connected to linking box 20 and control unit 45 of the cryosurgery device.

Preferably, control unit 45 includes a mobile housing 36 for accommodating at leas one gas containers 34, the gas container for providing a specific gas of high pressure to operating members 2. As shown, housing 36 includes an interface element 30 having connection sites 28 for communicating gas lines 32 arriving from gas container 34 with flexible gas lines 26. Gas container 34 may include a cooling gas such as argon, nitrogen, air, krypton, $CF_4$ xenon, or $N_2O$. A second gas container 34 may be provided for a heating gas such as helium.

Attention is now drawn to FIG. 2, which presents a simplified schematic of a cryosurgery device according to methods of prior art.

As shown in FIG. 2, an operating member 2 includes an elongated operating tip 74 for freezing a patient's tissue. Operating tip 74 includes at least one passageway 76 extending therethrough for providing gas of high pressure; to a heat exchanger and a Joule Thomson orifice 78 located at the end of operating tip 74, the orifice for passage of high pressure gas therethrough so as to heat or cool operating tip 74, depending on the type of gas used. Gases which may be used for cooling include argon, nitrogen, air, krypton; $CF_4$ xenon, or $N_2O$. Gases which may be used for heating include helium.

When a high pressure cooling gas such as argon flows through the heat exchanger and expands through orifice 78 it cools and may partially liquefy so as to form a cryogenic pool within chamber 82 of operating tip 74. The cooled expanded gas and/or cold liquefied gas effectively cools surface 80 of operating tip 74. The surface 80 of operating tip 74 is preferably made of a heat conducting material such as metal for effectively freezing the patient's tissue. When a high pressure heating gas such as helium expands through orifice 78 it heats chamber, 82, thereby heating surface 80 of operating tip 74.

Operating tip 74 includes at least one evacuating passageway 79 extending therethrough for evacuating gas from the operating tip to atmosphere. As shown in the figure, passageway 76 is preferably in the form of a spiral tube wrapped around passageway 79.

Further, operating tip 74 includes at least one thermal sensor 75 for sensing the temperature within chamber 82, the wire of which extending through evacuating passageway 79, or a separate passageway.

Operating tip 74 is connected to a holding member 72 for holding by a surgeon. Holding member 72 includes a plurality of switches 71a, 71b, 71c and 71d for manually controlling operating tip 74 by a, surgeon. Switches 71a, 71b, 71c and 71d may provide functions such as on/off, heating, cooling, and predetermined cycles of heating and cooling by selectively and controllably communicating passageway 76 with an appropriate gas container 34 including a cooling or a heating gas.

As shown in FIG. 1, each of operating members 2 is connected via a flexible connecting line 4 to a connecting site 8 on interface element 6. Preferably, each of operating members 2 includes a linking element 7 for attachment to a connection site 8.

Preferably, evacuating passageway 79 extends through connecting line 4 such that the outgoing gas is evacuated through an opening located at linking element 7.

As shown in FIG. 1, positioned on housing 36 are a microprocessor 43, a display element 42, and a keyboard 44. Microprocessor 43 controls the operation of the cryosurgery device according to predetermined operating conditions provided by the surgeon. Keyboard 44 may be used for programming the operating conditions and for reading selected data. Display element 42 is used for displaying data relating to the status of each of the operating members 2 and other updated data on the surgery being performed. Further, display element 42 may provide information relating to the medical record of a specific patient.

Switches 71a, 71b, 71c and 71c of operating member 2 (FIG. 2) are electrically connected to microprocessor 43 so as to enable manual control of operating tip 74. Further, thermal sensor 75 is electrically connected to microprocessor 43 so as to enable continuous monitoring and control of the temperature within chamber 82. An embodiment for providing controlled temperature changes within chamber 82 is disclosed in U.S. Pat. No. 5,540,062. Further features of a cryosurgery device according to methods of prior art, including specific features of control unit 45 and operating member 2 are disclosed in U.S. Pat. Nos. 5,522,870 and 5,603,221.

As shown in FIG. 1, a conventional MRI display element 56 is positioned within MRI room 54 for displaying an image representing the site of operation so as to provide guidance to a surgeon. Display element 56 preferably includes a video card and is electrically connected to microprocessor 43 located externally to MRI room 54 via an electrical connection (not shown), which electrical connection may be extended through underground lines 12 and linking box 20. Such configuration enables to provide the surgeon an image identical to the image displayed on external display element 42, which image including information relating to the operation of the cryosurgery device. Display element 56 is provided with a switching member 57 for enabling a surgeon to select the required image and thus to monitor the progress of the surgical process via first and second channels, wherein the first channel provides an MRI guidance and the second channel provides current information relating to, the cryosurgery device. According to another embodiment (not shown), a second display element is provided within MRI room 54 so as to enable a surgeon to simultaneously monitor the surgical process and observe the operation of the cryosurgery device.

Figure 3:
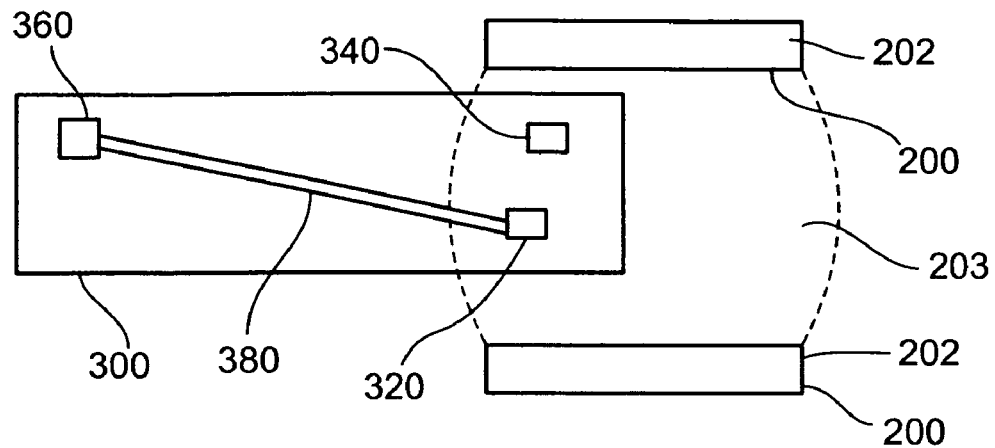
FIG. 3 is a simplified schematic of an MRI-guided, cryosurgery system, according to an embodiment of the present invention.

Attention is now drawn to FIG. 3, which presents a simplified schematic of an MRI-guided cryosurgery system, according to an embodiment of the present invention.

FIG. 3 presents a system 400 which comprises an MRI apparatus 200 operable to generate MRI images of at least a portion of a body of a patient during a cryosurgery procedure, and an MRI-compatible cryosurgery module 300.

MRI apparatus 200 comprises the various well-known internal components of MRI systems, including magnets 202 creating an MRI magnetic environment 203.

MRI-compatible cryosurgery module 300 is a cryosurgery module operable to, perform cryoablation of tissues in a body of a patient, while at least a portion of the body of that patient is within MRI magnetic environment 203 and during magnetic resonance imaging, of that patient. Cryosurgery module 300 comprises an MRI-compatible intervention module 320, an MRI compatible cryosurgery control module 340, a cryosurgery support module 360 preferably positioned outside of MRI magnetic environment 203, and a fluid supply conduit 380 joining cryosurgery support module 360 to components of intervention module 320.

Figure 4:
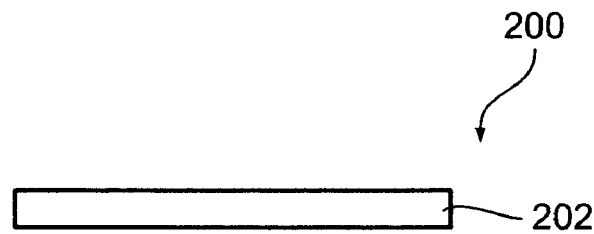
FIG. 4 is a simplified schematic of MRI apparatus, according to an embodiment of the present invention.
Figure 4:
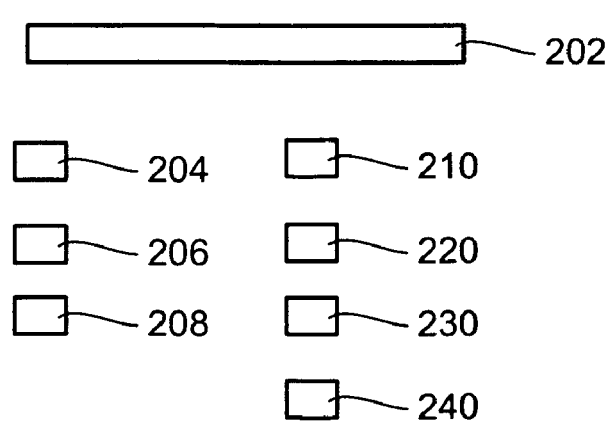

Attention is now drawn to FIG. 4, which is a simplified schematic of MRI apparatus 200, according to an embodiment of the present invention. As seen in FIG. 4, MRI apparatus 200 comprises the various well-known internal components of MRI systems, including magnets 202 creating an MRI magnetic environment 203, an electromagnetic pulse generator 204, receiving antennas 206, a data collection and interpretation module 208, and other well-known MRI parts and features MRI display module 210 is a display module-operable to display MRI-generated images of a portion of a body of a patient MRI command interface module 220 is a user interface operable to receive operating commands from a surgeon or other human operator, which commands control various aspects of operation of MRI apparatus 200.

MRI apparatus 200 also comprises two analytical modules not typically present in prior art MRI systems. A temperature observation module 230 is operable to glean body tissue temperature information from MRI-generated data, and optionally to present such information on MRI display module, 210. In a preferred embodiment, temperature observation module 230 is operable to glean body, tissue temperature information from frozen tissue. An ablation border estimation, module 240 is operable to analyze temperature data observed by temperature observation module 230, to collect such observed body temperature data over time, and to estimate, based on stored algorithmic methods for interpretation of that stored body temperature data, body, tissue temperatures not directly observable in the MRI observed data. Temperature observation module 230 and ablation border estimation module 240 may be integrated with general-purpose data collection and interpretation module 208, or may be embodied as independent software and/or hardware units. Temperature data observed by temperature observation module 230 and temperature data estimated by ablation border estimation module 240 may optionally be displayed on MRI display 210 and may be integrated with a display of body tissues presented on display 210. Alternatively, observed and estimated temperature data, and an estimated position of a border of an ablation volume deduced; from that estimated temperature data, may be utilized as a basis for calculating recommendations to, a surgeon and/or commands to cryosurgery apparatus 300, as will be shown hereinbelow.

Figure 5:
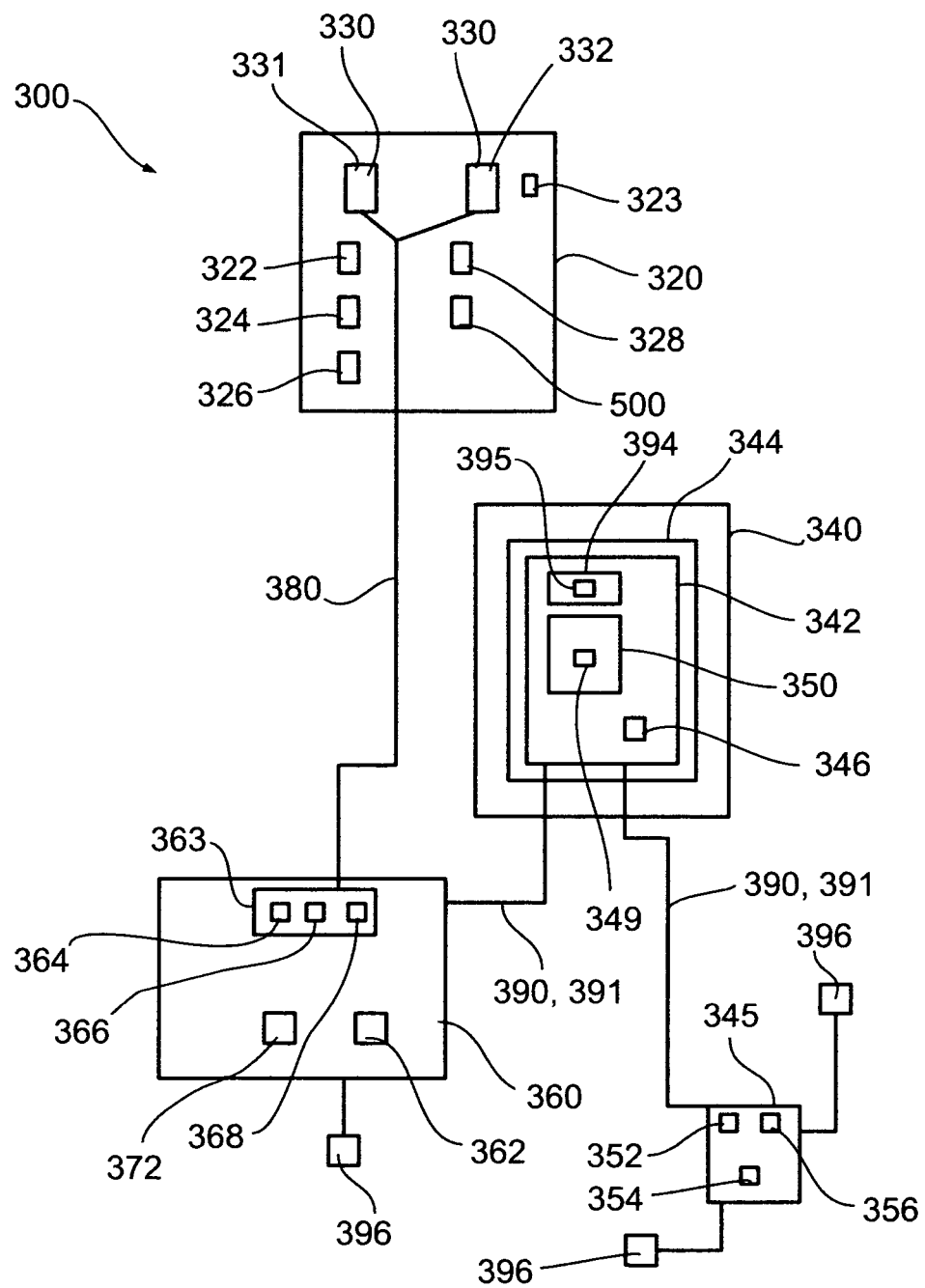
FIG. 5 is a simplified schematic of MRI compatible cryosurgery module, according to an embodiment of the present invention.

Attention is now drawn to FIG. 5, which is a simplified schematic of MRI-compatible cryosurgery module 300, according to an embodiment of the present invention.

Cryosurgery module 300 includes an MRI-compatible intervention module 320. Intervention module 320 comprises at least one and preferably a plurality, of MRI-compatible cryoprobes 330. Cryoprobes 300 may be a Joule-Thomson cryoprobes 331, which cool by rapid expansion of a compressed gas through a Joule-Thomson orifice, similar to the cryoprobe presented in FIG. 2 and described in detail hereinabove alternatively, cryoprobe 330 may be an evaporatively cooled cryoprobe 332, which cools by evaporation of a liquefied gas, according to structural and functional details well known in the art. Alternatively, cryoprobe 300 may be any other cryoprobe cooled through use of a refrigerant fluid.

Cryoprobe 330 is operable to be inserted into the body of a patient and to cryoablate tissues therein. Intervention module 320 preferably includes a plurality of cryoprobes 330, and may include a variety of additional MRI-compatible surgical tools whose use is complementary to, and compatible with, both MRI imaging and cryoablation technology. In particular, intervention module 320 may include an MRI-compatible template 322, useful for guiding insertion of a cryoprobe or a plurality of cryoprobes into a body of a patient, an MRI-compatible cryoprobe introducer 324 useful for inserting a plurality of cryoprobes into a body of a patent in a single insertion, an MRI-compatible trocar 326 useful for introducing a cryoprobe or other surgical tools into a body cavity of a patient, an MRI-compatible guide-wire module 328 useable for guiding penetration of a cryoprobe within a body conduit, MRI-compatible thermal sensors 500 which may be positioned inside or outside cryoprobes 330 or may be independently insertable into the body of a patent, and other well-known surgical tools for implementing and enhancing cryosurgery procedures. An MRI-compatible servomotor 323 may be provided for automated control of insertion or placement of cryoprobes 330 in the body of a patient. In a preferred embodiment, a template 322 is used to guide insertion of a cryoprobe in a selected direction, and a servomotor 323 (e.g., a stepper motor) is provided to advance or retract a cryoprobe 330 in along that selected direction, under control of cryosurgery control module 340, as will be discussed in further detail hereinbelow.

MRI-compatible elements mentioned in herein are constructed of materials presenting no interaction or minimal interaction with the magnetic field and electromagnetic pulses of the MRI imaging system. Inconel and titanium, for example, are known to be such materials.

Cryosurgery module 300 further includes a cryosurgery control module 340. Control module 340 includes a user interface 350 operable to receive commands from human operator. Control module 340 is optionally operable to communicate received commands directly to cryosurgery support module 360. In a preferred embodiment, however, cryosurgery control module 340 is operable to perform algorithmic interpretation of received operator commands in accordance with stored algorithmic rules of interpretation, which rules may take into account data received from sensors such as thermal sensors 500 within a body of a patient, pressure sensors and/or gas flow sensors 362 within support module 360, and data received and interpreted by MRI data collection and interpretation module 208, data from temperature observation module 230, calculations performed by ablation border estimation module 240, and data from other sources. In this preferred embodiment control module 340 is further operable to issue operational commands to support module 360 based on algorithmic interpretation of received operator commands and received or calculated data. (Use of MRI-based information useful for detecting or estimating the three-dimensional contours of an ablation volume is discussed in detail below.)

Control module 340 comprises a shielded electrical circuit 342. Shielded circuit 342 is enclosed in one or preferably several layers of MU-metal (μ-metal) shielding 344, and is thereby shielded from influence by the strong magnetic field generated by magnets 202, and from influence by electromagnetic pulses generated by electromagnetic pulse generator 204. Further, MU-metal shielding 344 prevents circuit 342 from broadcasting magnetic fields. (e.g., from electrical transformers) and/or electromagnetic signals (e.g. from rapid switching circuits of a computer CPU) which might otherwise influence signals received at MRI receiving antennas 206 and thereby cause distortion of MRI data and consequent distortion of MRI images produced by MRI module 300.

Control module 340 preferably comprises a cryosurgery module status display 346 and a cryosurgery user interface 350 through which a human operator can input commands, through control module 340, to cryosurgery module 300. In a preferred embodiment, user interface 350 comprises a voice recognition module 349, enabling a surgeon to input operational commands to control module 340 orally, permitting hands-free operation of control module 340 for a surgeon whose hands are typically required for various surgical tasks. Embodiments of the present invention including voice recognition module 349 may comprise portions of control module 340 which are not MRI-compatible and which are designed for placement outside an MRI magnetic environment, since the presence of voice recognition module 349 enables a surgeon to input commands to control module 340 even when control module 340 is physically distanced from the surgeon and his patient.

Cryosurgery module display 346 also preferably comprises text-to-speech algorithms enabling control module 340 to optionally communicate status information to a surgeon orally as was by visual display.

In a particularly preferred embodiment, cryosurgery module status display 346 and MRI display module 210 are combined in a common display 502 operable to display both MRI images and cryosurgery module status. Similarly, in a particularly preferred embodiment, cryosurgery user interface 350 (shown in FIG. 1) and MRI command interface module 220 are combined in a common user interface 504 (shown in FIG. 1), interface 504 being ergonomically designed to receive input both to MRI imaging module 200 and to cryosurgery module 300.

In one preferred configuration, shielded electrical circuits 342 may include all electronic components of control module 340. In an alternative configuration, control module 340 may be divided into a shielded portion which includes shielded circuit 342, and an unshielded portion 345 which may be positioned outside of MRI magnetic environment 203. It may be convenient, for example, to position cryosurgery display 346 and cryosurgery user interface 350 within MU-metal shielding 344, yet position computation components such as a CPU 352, memory 354, data recording unit 356 and other computational elements in proximity to cryosurgery support module 360 and outside MRI magnetic environment 203.

Cryosurgery module 300 further includes a cryosurgery support module 360. Support module 360 comprises a supply of coolant fluid 363, which coolant fluid is operable to cool cryoprobes 330 of intervention module 320. If cryoprobe 330 is an evaporatively cooled cryoprobe 332, coolant fluid 362 may be a liquefied gas 364 such as $N_2$ or $NO_2$ or any other suitable liquefied gas. Liquefied gas 364, when caused to flow to an evaporatively cooled cryoprobe 332, is operable to cool cryoprobe 332 by evaporation. In an alternative preferred embodiment, cryoprobe 330 may be a Joule-Thomson cryoprobe 331, and coolant fluid 362 may be a compressed cooling gas 366, which gas is operable to cool a Joule-Thomson cryoprobe 331 by rapid expansion of cooling gas 366 through a Joule-Thomson orifice within cryoprobe 331. Cryosurgery support module 360 may further comprise fluid means or other means for heating cryoprobes 330, such as a compressed heating gas 368 operable to heat Joule-Thomson cryoprobe 331 by expansion of heating gas 368 through a Joule-Thomson orifice therein. Support module 360 may also include other heating means, such as an electrical current source 372 operable to heat a cryoprobe 330 by electrical heating.

Cryosurgery support module 360 is operable to supply coolant fluid to a fluid supply conduit 380 in response to a command received from control module 340. Fluid supply conduit 380 provides a channel for transport of cooling fluid from cooling fluid supply 363 to cryoprobes 330. Distal portions of supply conduit 380, which portions are designed to be used in proximity to a patient and within-MRI magnetic environment 203, are constructed of MRI-compatible materials.

Data transmission between control module 340 and cryosurgery support module 360, or between two parts of control module 340, is preferably provided by a shielded cable 390, a cable preferably shielded with MU-metal, thereby avoiding unwanted magnetic and electromagnetic interactions between cable and MRI magnetic fields and alternate preferred embodiment, optical communication may be provided, either by implementing cable 390 as a fiber-optic cable 391, or by free-path light communication, such as may be provided by infra-red communications device 394. Infra red communications device 394 preferably comprises a first IR communications device 395 which is MRI-compatible and in shielded data communication with cryosurgery; user interface 248, and a plurality of second IR communications devices 396, which, may be MRI-compatible or may alternatively be positioned outside the MRI magnetic environment, operable to communicate with first IR communications, device, 395 and electronically to communicate with other parts of system 400. A plurality of interoperable second IR communications devices 396 is desirable, since communications among IR communications devices is limited to line of sight providing a plurality of second IR devices 396 each of which is operable to communication with first IR device 395 enables first IR device 395 to communicate when positioned at various directions and angles within the operating theatre environment. Similarly, data communication to and from intervention module 320 (e.g. reporting data from sensors, or transmitting commands to servomotors), is also preferably optical, or electrical and shielded, and electrical supply lines to intervention module 320 (e.g., for optional electric heating of cryoprobes, or to supply power to servomotors) are also shielded.

Figure 6A:
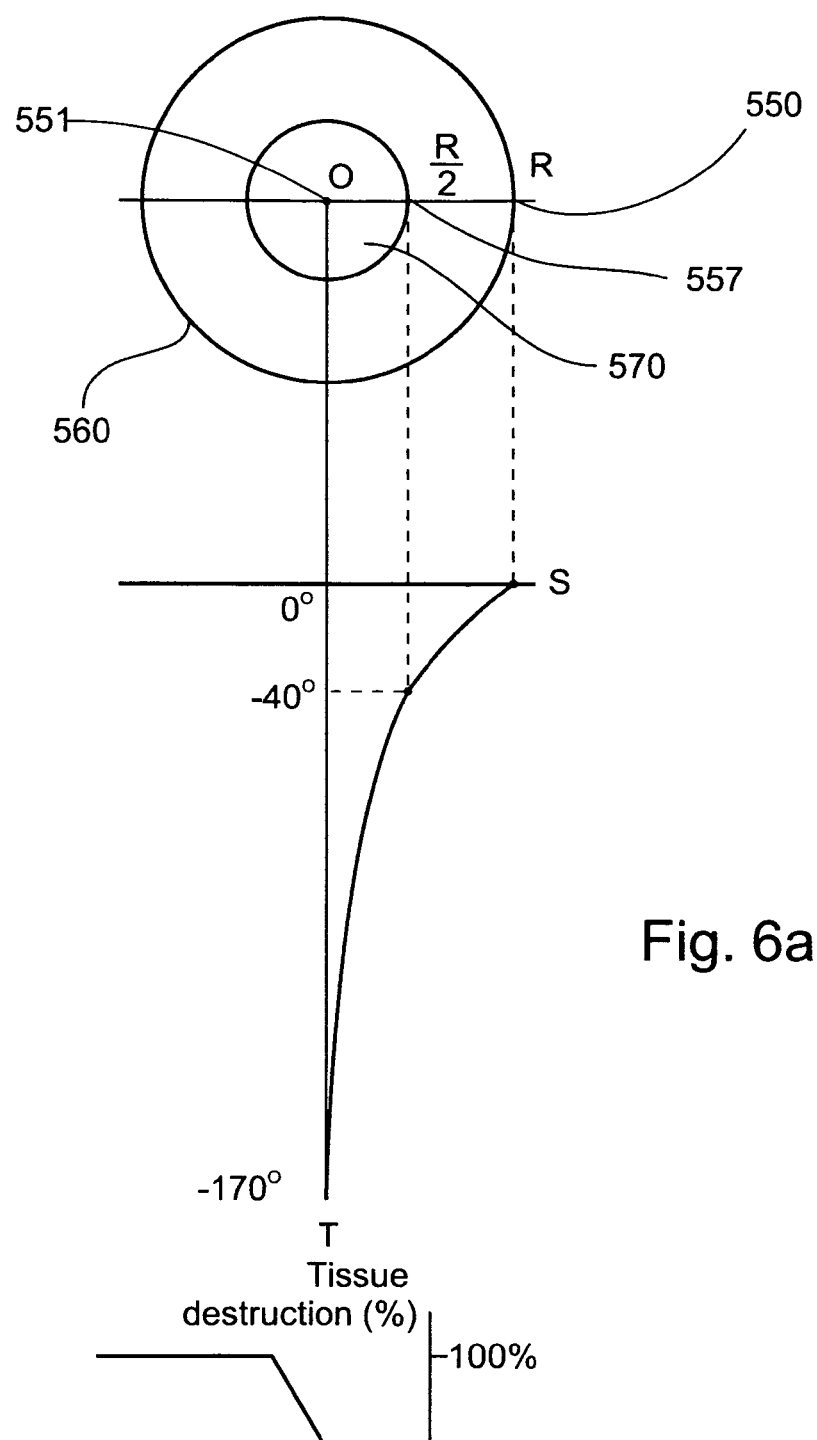
FIG. 6A is an illustration of a temperature distribution profile across an ice-ball 560 formed at the tip of a cryosurgical probe.

Attention is now drawn to FIG. 6A, which is an illustration of a temperature distribution profile across an ice-ball 560 formed at the tip of a cryosurgical probe. As shown, the temperature at a surface 550 of the ice-ball is 0° C. The temperature declines exponentially towards a center 551 of the ball where it preferably reaches the value of –170° C., such that an isothermal surface 557 of about –40° C. is typically located within the ice-ball at the half way between the center of the ball and its surface. Thus, if the ice-ball features a radius R, then the radius of the –40° C. isothermal surface 557 is about R/2. Thus, isothermal surface 557 forms a border of a volume of reliable destruction of tissues, termed herein an "ablation volume", here designated 570.

Figure 6B:
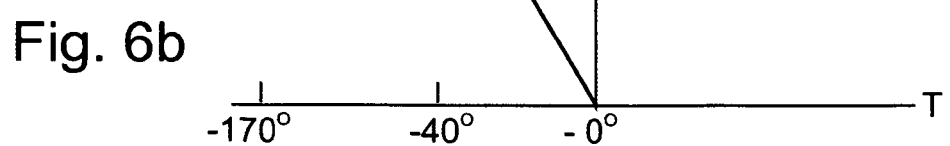
FIG. 6B is a graph showing the effectiveness of a cryosurgical treatment (given in percentage of tissue destruction) as a function of temperature.

Attention is now drawn to FIG. 6B, which is a graph showing the effectiveness of a cryosurgical treatment (given in percentage of tissue destruction) as a function of temperature. As shown, the temperature required for effectively destroying a tissue is at least about –40° C. Accordingly, in order to effectively destroy a tissue, the isothermal surface of –40° C. (shown in FIG. 6A) should be placed at the periphery of the treatment target so that the entire volume of the treatment target is exposed to cold of –40° C. or below. Adjacent healthy tissues and organs within the external portion of the ice-ball are thereby unavoidably exposed to cold of between –40° C. and 0° C. Exposure of healthy tissues to such temperatures usually causes substantial damage thereto, which damage may result in temporary or permanent impairment of functional organs.

The temperature of –40° C. is presently considered a reliable border of an ablation volume, according to prevalent expert opinion and common contemporary surgical practice, but of course that number may vary with the gathering of additional clinical experience and experimental evidence. There is already evidence that the degree of cooling required for total tissue destruction depends to some extent on whether the tissue is frozen only once or is frozen, thawed, and refrozen, and depends also on the speed of freezing; and speed of thawing. In any case it is to be understood that the –40° C. temperature is here presented as an example of an isotherm defining a border of an ablation volume, and that isotherms at other temperatures, or borders of the ablation volume depending on factors additional to pure temperature measurement (e.g., borders calculated as a function of temperature, time frozen, speed of thawing, etc.) may be calculated.

As explained in the background section hereinabove, it is desirable to avoid damage to healthy tissue surrounding an ablation target, and it is desirable (in the case of malignancies, it is essential) that all of an, ablation target be included within an ablation volume during cryosurgery.

In the case of a single probe cooling homogeneous material, the position and size and shape of an ablation volume is easily determined, as shown in FIG. 6A. However, modern cryosurgical practice typically involves situations more complex than this simple theoretical model. In contemporary practice a plurality of cryoprobes is often used, heating is often used in conjunction with cooling to protect sensitive tissues near pathological an tissue in the vicinity of operating cryoprobes is not homogeneous.

System 400 provides means for observing or estimating an ablation target border. Although currently available commercial MRI equipment does not provide possibility of thermal measurement of frozen tissues, such measurement appears to be theoretically possible, thus it is expected that MRI systems will become available which will provide a temperature readout from frozen tissue, using techniques similar to those which provide temperature readout from non-frozen tissue under MRI analysis today. Temperature observation module 230, presented in FIG. 4, provides this function.

Alternatively, it is possible using currently commercially available MRI equipment to estimate (calculate) a three-dimensional shape and position of an ablation border. This function is provided by ablation border estimation module 240, presented in FIG. 4.

Figure 7:
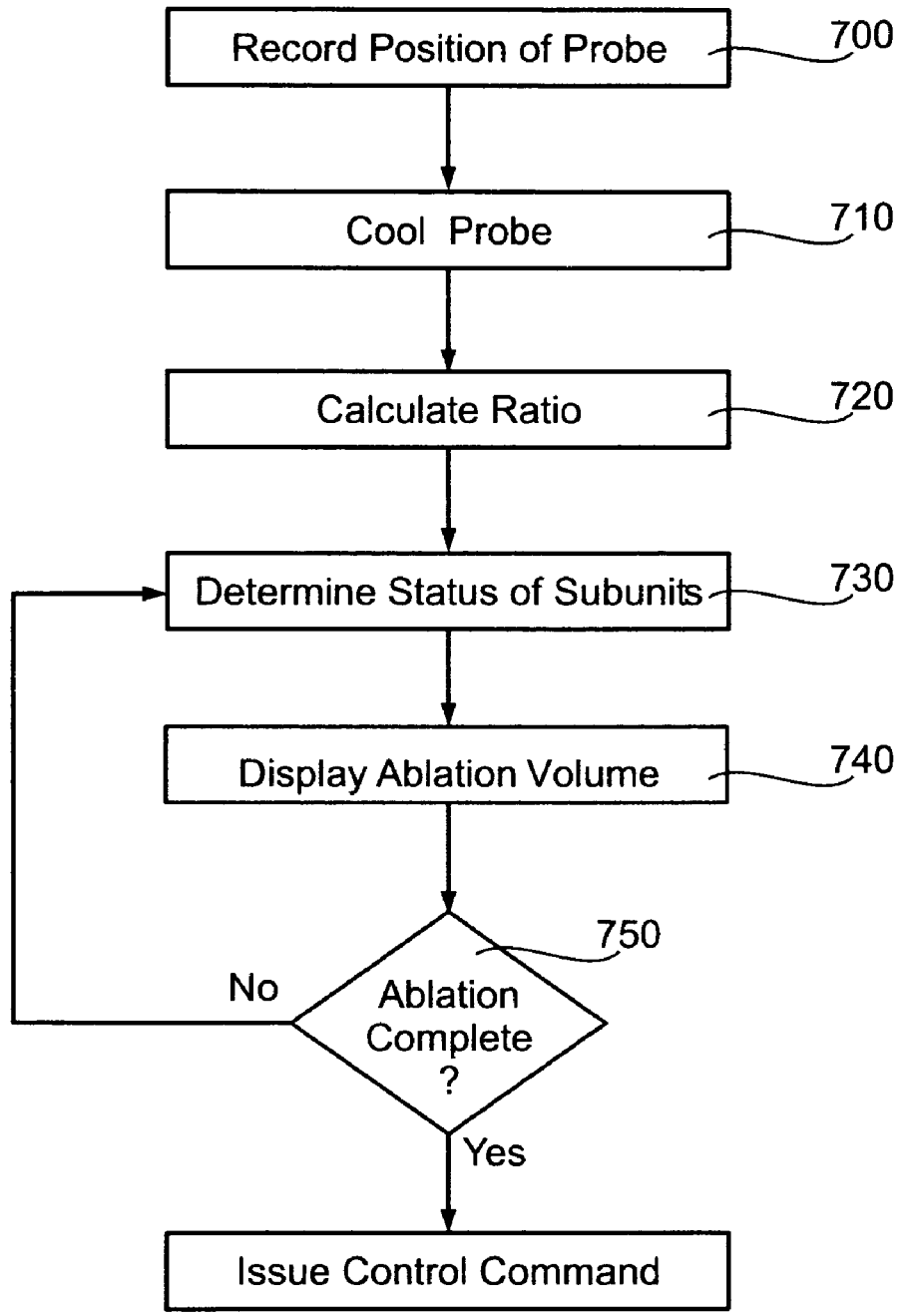
FIG. 7 is a simplified flowchart of a procedure for estimating three-dimensional size and shape of an ablation volume, according to and embodiment of the present invention.

Attention is now drawn to FIG. 7, which is a simplified flowchart of a procedure for estimating three-dimensional size and shape of an ablation volume, according to and embodiment of the present invention. In alternative configurations the steps outlined in FIG. 7 may be though of as being executed by ablation border estimation module 240, or by cryoablation control module 340, or by some combination of the two.

At step 700, position of a cryoprobe 300 is noted, prior to freezing of tissues adjacent to that probe. At step 710, cooling of probe 330 begins, and standard MRI imaging and analysis tools are used by data collection and interpretation module 208, preferably on a continuous real-time basis, to calculate and report, in three-dimensional space, position and shape of an iceball which forms around cryoprobe 330.

At step 720, following principles presented hereinabove with reference to FIGS. 6A and 6B, a ratio is calculated for estimating the position of an ablation border the distance of that ablation border from a cryoprobe 330 is expressed as a proportion of a distance from cryoprobe 330 to a nearest observed border of an ice-ball formed around cryoprobe 330. For example, using the conditions and temperatures defined in the above discussion of FIGS. 6A and 6B, R/2 (50%) would be the calculated ratio. Step 720 may of course be performed prior to steps 710 if desired.

At step 730, the volume of tissue contained within an iceball 560 formed around a cryoprobe or plurality of cryoprobes 330 is digitally subdivided and its subdivisions examined to determine which subdivisions are within and which subdivisions are outside a calculated border of an ablation volume. Reference points for any such subunit are taken to be a) that position on a cooling portion of a cryoprobe 330 closest to that subunit, and b) that portion of an outside border of iceball 560 closest to that subunit. If a selected ratio of 50% is used, as described in the previous paragraph, then a subunit closer to the closest portion of a cooling cryoprobe than to the closest border of iceball 560 is determined to be within an ablation volume, and, a subunit closer to the edge of iceball 560 than to the nearest cooling portion of cryoprobe 330 is judged to be outside the ablation volume. This calculation can of course be adapted for isotherms other than −40° for cryoprobe temperatures other than −170°, and for other considerations such as duration of freeze, speed of thaw, etc. Inn general, step 730 consists of determining for each subunit whether it is within an ablation volume by determining a first distance, distance of the subunit from a nearest cooling portion of a cryoprobe 330, and a second distance, distance of the subunit from a nearest border of the iceball, and concluding that the subunit is within the ablation volume if the first distance divided by a sum of the first and second distances is less than the selected ratio, and concluding that said subunit is outside the ablation volume if the first distance divided by the sum of the first and second distances is greater than the selected ratio.

Step 730 preferably includes making the calculation described in the previous paragraph for each subunit of iceball 560, subunits preferably being chosen to be of a size convenient for high resolution imaging of ablation volume 570.

At optional step 740, ablation volume 570 may be displayed to a surgeon, preferably in an integrated display also showing iceball borders and other anatomical features, and optionally also showing position of cryoprobe 330 as determined prior to freezing. Such a display can be of invaluable assistance to a surgeon in determining whether a cryoprobe has been optimally placed, and in determining the appropriate moment for terminating cooling, e.g., when a displayed ablation volume has adequately covered a pre-defined ablation target.

At alternative optional step 750, information generated at step 730 is used to directly control operation of cryoprobe 330. If an ablation target has been defined and three-dimensional size and position of an ablation volume 570 has been determined as described in step 730, it is easy to determine by algorithmic comparison of that defined ablation target to that calculated size and position of ablation volume 570 whether the predefined ablation target has in fact been ablated. At step 750 this determination is made. Determination that a predefined ablation target has in fact been ablated is thus a "trigger event", an event which triggers a further response of the system.

Such a trigger event may for example cause emission of a warning or notification to an operating surgeon, informing him that ablation has been achieved and recommending that he initiate a change in an ongoing procedure (e.g., that he switch from cooling to heating of the cryoprobes.) In a preferred embodiment of the present invention, a trigger event such as a determination that cryoablation of a predefined target has been achieved may result directly in a system-controlled change in an ongoing procedure without requiring intervention of a surgeon at optional step 760, cryoablation control module 340 can operational command to cryoablation support module 360, based on the determination made in step 750. For example, if it is determined at step 750 that a predefined ablation target has in fact been ablated, cryoablation control module 340 can issue an operational command to support module 360, commanding that cooling gas flow be stopped and heating gas flow be started, thereby switching cryoprobe 330 from cooling operation to thawing operation.

The device whose operation is described in FIG. 7 can also be used to make early determination of the optimality of a given position of a cryoprobe or of a plurality of cryoprobes. Since it is desirable to avoid destruction or damage of healthy tissue to as great an extent as possible consistent with entire destruction of a predefined ablation target, it is desirable that cryoprobes be optimally placed with respect to the ablation target. A surgeon naturally uses all available information (images of the probes in place, images of the lesion) to place probes in what he hopes will be an optimal position within the ablation target before commencing the freezing process, since freezing has begun the probe is immobilized within the body tissues until thawing begins. If the probe or probes are not optimally placed, freezing (and the ablation volume) will be "off-center", i.e., undesirably displaced with reference to the target. In practice, such misplacement results in a first side of an ablation target being completely ablated while a second side requires further freezing. Since the cryoprobes freeze all sides simultaneously, the result is unnecessary tissue destruction on the first side of the target, necessitated by the need to continue freezing the second side. When a surgeon discovers such a situation he may choose to thaw the tissues, displace the cryoprobe or cryoprobes, and refreeze the tissue. However, this time-consuming process is inconvenient for the surgeon and undesirable for the patient, as it lengthens the surgical process.

The estimation/observation procedures outlined in FIG. 7 provide means to facilitate correct positioning of cryoprobes 330, thereby minimizing undesired freezing, thawing, repositioning and re-freezing of tissues, and also avoiding the equally undesirable alternative of not repositioning an off-center probe and thereby causing unnecessary damage to healthy tissue. When freezing begins, MRI images provide accurate information concerning the size and shape of a iceball 560 as iceball 560 begins to grow within the body tissue. A simple adaptation of the algorithmic estimation method described above can provide an early warning of non-optimally positioned cryoprobes, as iceball growth in various directions is observed and ablation volume growth is observed or estimated, and these are compared to the size, shape, and position of a predefined ablation target. When the system determines that a growing iceball is not optimally placed with respect to an ablation target, this too can be defined as a "trigger event", resulting in issuing a warning to a surgeon and/or to issuing heating and/or cryoprobe displacement commands to module 200, these warnings and/or thawing and repositioning commands enabling repositioning of cryoprobes 330 early in the freezing process, rather than after extensive freezing has taken place. Such a procedure is faster and easier than repositioning of cryoprobes after extensive freezing has already taken place and is preferable to unnecessary and undesirable freezing of healthy tissues caused by inappropriate or non-optimal positioning of cryoprobes.

Thus, output of temperature observation module 230 and of ablation border estimation module 240 may be used to trigger-warnings and recommendations to a surgeon. In a preferred embodiment, some control functions may be executed by the control module 340 directly, preferably with possibility of manual override by a surgeon. Thus, once the ablation target has been defined and cooling started, termination of the cooling process (or transfer from cooling operating to heating operation, or from heating back to cooling, as predetermined by an ablation protocol) could be entirely controlled by controller 340, according to the principles described in the preceding paragraphs, wherein MRI data is repeatedly analyzed to determine whether an ablation volume has included all of an ablation target. Similarly, optimal placement of a cryoprobe may also be subject to direct control of positioning by controller 340. A servomotor 323, shown in FIG. 5 is operable to receive positioning commands from controller 340 and displace an inserted cryoprobe 330 at least in one dimension. For example, template 322 may be used to guide a cryoprobe 330 along a one-dimensional path, and servomotor 323 may be used to advance or retract cryoprobe 330 along that path. The techniques described above for early determination of optimality or non-optimality of placement of cryoprobe 330 can then be used to generate thawing commands to cryoprobe module 200, followed by cryoprobe movement commands to servomotor 323 causing displacement of cryoprobe 330 in a desired direction, thereby automatically optimizing placement of cryoprobe 330.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A cryosurgery system comprising:
   (a) an intervention module which comprises at least one cryoprobe operable to be inserted into the body of a patient and to cryoablate tissues therein;
   (b) an ablation border estimation module which uses information received from at least one of a group consisting of an imaging modality and a thermal sensor to estimate a border of an ablation volume within a body of a patient, said border estimation module being configured to:
      (i) record a position of a cryoprobe within tissues of a patient's body prior to freezing of body tissues;
      (ii) record position of borders of an iceball formed during freezing of body tissues;
      (iii) utilize a distance ratio to determine status of sub-units of tissue within said iceball;
   (c) a cryosurgery control module which calculates a command for said cryosurgery support module, said calculation being based at least in part on said estimated ablation volume border;
   (d) a cryosurgery support module configured to control delivery of a coolant fluid to a fluid supply conduit in response to commands received from said control module; and
   (e) a fluid supply conduit operable to deliver a coolant fluid from said support module to said cryoprobe.

2. The system of claim 1, wherein said intervention module is MRI-compatible and said at least one cryoprobe is MRI-compatible, and wherein said ablation border estimation module uses information received from an MRI system.

3. A cryosurgery system comprising:
   (a) an intervention module which comprises at least one cryoprobe operable to be inserted into the body of a patient and to cryoablate tissues therein;
   (b) an ablation border estimation module which uses information received from at least one of a group consisting of an imaging modality and a thermal sensor to estimate a border of an ablation volume within a body of a patient;
   (c) a cryosurgery control module which calculates a command for said cryosurgery support module, said calculation being based at least in part on said estimated ablation volume border, said cryosurgery control module being configured to compare said estimated cryoablation volume border to a predetermined cryoablation target to determine whether said predetermined cryoablation target is contained within said cryoablation volume;

(d) a cryosurgery support module configured to control delivery of a coolant fluid to a fluid supply conduit in response to commands received from said control module; and (e) a fluid supply conduit operable to deliver a coolant fluid from said support module to said cryoprobe.

4. The system of claim 3, wherein said cryosurgery control module notifies a surgeon if said cryoablation target is determined to be contained within said cryoablation volume.

5. The system of claim 3, wherein said cryosurgery control module issues a command to said cryosurgery support module if said cryoablation target is determined to be contained within said cryoablation volume.

6. A system according to claim 1 or claim 3, wherein said intervention module further comprises a plurality of cryoprobes.

7. A system according to claim 1 or claim 3, wherein said intervention module further comprises an MRI-compatible template operable to guide insertion of said cryoprobe into said body of said patient.

8. The system of claim 7, further comprising an electromechanical device operable to move said cryoprobe within said body of said patient.

9. A system according to claim 1 or claim 3, wherein said intervention module further comprises an MRI-compatible guide wire operable to be positioned within said body of said patient, and operable to guide positioning of said cryoprobe within said body of said patient.

10. A system according to claim 1 or claim 3, wherein said intervention module further comprises a thermal sensor operable to be positioned at a selected position with said body of said patient and to report temperature of said body at said selected position.

11. A system according to claim 1 or claim 3, wherein said cryoprobe comprises a thermal sensor operable to report temperatures within said cryoprobe.

12. A system according to claim 1 or claim 3, wherein said cryoprobe comprises a thermal sensor operable to report temperature external to said cryoprobe.

13. A system according to claim 1 or claim 3, wherein said cryoprobe is at least partially constructed of MRI-compatible material.

14. A system according to claim 1 or claim 3, wherein said cryosurgery control module comprises an interface for receiving operational commands from an operator.

15. A system according to claim 1 or claim 3, wherein said cryosurgery control module is constructed of MRI-compatible materials and is operable to send commands to said cryosurgery support module while positioned in proximity to a surgeon and within an MRI environment.

16. The system of claim 15, wherein said cryosurgery control module is operable to receive and interpret oral commands from a human operator.

17. The system of claim 16, wherein said cryosurgery control module is operable to be positioned external to an MRI environment and to receive and interpret oral commands from a human operator positioned within said MRI environment.

18. A system according to claim 1 or claim 3, further comprising a display.

19. The system of claim 18, wherein said display is operable to display information pertaining to operational status of said cryoprobe.

20. The system of claim 18, wherein said display is operable to display information gleaned from sensors positioned within said body of said patient.

21. The system of claim 18, wherein said display is MRI-compatible.

22. The system of claim 18, wherein said display is operable to display information pertaining to operational status of said cryosurgery support module.

23. A system according to claim 1 or claim 3, wherein said cryosurgery support module comprises a source of high-pressure cooling gas.

24. A system according to claim 1 or claim 3, wherein said cryosurgery support module comprises a source of high-pressure heating gas.

25. A system according to claim 1 or claim 3, wherein said cryosurgery support module is operable to selectively deliver to said fluid conduit a gas selected from a group consisting of a high-pressure heating gas and a high-pressure cooling gas.

26. The system of claim 3, wherein said intervention module is MRI-compatible and said at least one cryoprobe is MRI-compatible, and wherein said ablation border estimation module uses information received from an MRI system.

27. A system for cryosurgery, comprising:
(a) a cryosurgery apparatus useable to perform cryoablation of tissues in a body of a patient, said apparatus comprises:
   (i) an intervention module which comprises at least one cryoprobe operable to be inserted into the body of a patient and to cryoablate tissues therein;
   (ii) a cryosurgery control module operable to send commands to a cryosurgery support module;
   (iii) a cryosurgery support module which comprises a supply of coolant fluid, said support module being operable to deliver said coolant fluid to a fluid supply conduit in response to a command received from said control module; and
   (iv) a fluid supply conduit operable to deliver a coolant fluid from said support module to said cryoprobe;
(b) an MRI apparatus which comprises a display module operable to display to an operator images of a portion of a body of a patient, said images being generated by said MRI apparatus; and
(c) an analytical module which calculates a position of an ablation volume formed around a functioning cryoprobe within a body of a patient, said ablation volume being a volume of tissue located within a larger volume of frozen tissue within which cell functionality and structure are estimated to have been destroyed by cooling, said calculation being based on data gleaned from a plurality of images generated by said imaging modality, at least one of which shows a position of said cryoprobe prior to freezing of tissues and at least one of which shows a position of frozen tissue surrounding said ablation volume, said analytical module being configured to calculate said position of an ablation volume by
   (i) detecting and recording a position of said cryoprobe from an image created prior to creation of an iceball surrounding said probe;
   (iii) detecting and recording positions of borders of said iceball on said at least one image showing frozen tissue;
   (viii) digitally subdividing tissue within said iceball into subunits; and
   (iv) determining for each subunit whether it is within an ablation volume by calculating a first distance of said each subunit from a nearest cooling portion of said cryoprobe and a second distance of said each subunit from a nearest border of said iceball, and determining that said subunit is within said ablation volume if said first distance divided by a sum of said first and second distances is less than a selected distance ratio, and determining that said subunit is outside said ablation volume if said first distance divided by a sum of said first and second distances is greater than said selected distance ratio.

28. The system of claim 27, wherein said cryosurgery control module is constructed of MRI-compatible materials and is operable to send commands to said cryosurgery support module while positioned in proximity to a surgeon and within an MRI environment.

29. The system of claim 27, wherein said control module is configured to decide whether to issue a command to said cryosurgery support module, said decision being based on a comparison between a predetermined position of a cryoablation target and said calculated position of said ablation volume.

30. The system of claim 27, wherein said cryosurgery control module comprises a cryosurgery display operable to display operational status of elements of said cryosurgery apparatus.

31. The system of claim 30, further comprising a display module wherein said cryosurgery display and an MRI display module operable to display images generated by an MRI apparatus and showing a portion of a body of a patient, are integrated in a common display apparatus.

32. The system of claim 27, further comprising a temperature observation module operable to detect body temperature information from frozen tissue.

33. The system of claim 27, further comprising a temperature estimation module operable to estimate position of an isotherm at a pre-determined temperature within the body of a patient, based on detected position of at least one cryoprobe and detected position of an iceball border.

34. The system of claim 33, wherein said imaging modality is operable to display said estimated isotherm.

35. The system of claim 27, wherein said cryosurgery control module is further operable to generate a command to said cryosurgery support system, which command is based on an algorithmic response to said calculated position of said ablation volume.

36. The system of claim 35, wherein said generated command is operable to control cooling of said cryoprobe.

37. The system of claim 35, wherein said generated command is operable to control heating of said cryoprobe.

38. The system of claim 35, further comprising an electromechanical device for moving said cryoprobe within said body of said patient.

39. The system of claim 38, wherein said generated command is operable to control positioning of said cryoprobe by said electromechanical device.

40. The system of claim 27, wherein:
(a) said intervention module is MRI-compatible, said at least one cryoprobe is MRI-compatible, said cryosurgery control module is MRI-compatible and comprises a shielded electrical circuit, and at least a portion of said supply conduit is constructed of MRI-compatible materials; and
(b) said imaging modality comprises an MRI apparatus operable to generate and to display magnetic resonance images of a patient during a cryosurgery procedure; and
(c) said analytical module bases calculations on data gleaned from a plurality of MRI images at least one of which shows a position of said cryoprobe prior to freezing of tissues and at least one of which shows a position of frozen tissue surrounding said cryoprobe during cooling of said probe.

41. The system of claim 40, further comprising an integrated command module which comprises, in a common housing,
(a) said cryosurgery command module; and
an MRI command module operable to receive MRI operating commands from an operator and to modify MRI imaging performed by said MRI imaging apparatus according to said MRI operating commands.

42. A cryosurgery apparatus for performing cryosurgery in the body of a patient, comprising:
(a) a cryoablation system which comprises at least one cryoprobe;
(b) at least one imaging modality; and
(c) a control module which uses data drawn from analysis of both a first image created by a imaging modality prior to freezing of a portion of said body by said cryoprobe and a second image created by an imaging modality subsequent to freezing of a portion of said body by said cryoprobe to calculate an estimated temperature of tissue at a selected position within said frozen body portion and distant from an external border of said frozen body portion, the control module being configure to
(i) record a position of a cryoprobe within tissues of a patient's body prior to freezing of body tissues;
(ii) record position of borders of an iceball formed during freezing of body tissues; and
(iii) utilize a distance ratio to determine status of subunits of tissue within said iceball.

43. The system of claim 42, further comprising using said data to calculate an estimated position of a border of an ablation volume.

44. The system of claim 43, further comprising deciding whether to issue an an operative command to said cryoablation system based on a comparison between said estimated border of an ablation volume and a pre-defined cryoablation target border.

45. The system of claim 44, wherein said system is configured to issue said operative command when it is determined that said estimated border of an ablation volume includes all of a predefined treatment target volume within said body of said patient.

46. The system of claim 42, wherein said data drawn from analysis of said first image comprises information related to an observed position of said cryoprobe within said body.

47. The system of claim 42, wherein said data drawn from analysis of said second image comprises information relative to position of an iceball formed by cooling of a portion of said body by said cryoprobe.

48. The apparatus of claim 42, wherein said at least one cryoprobe is MRI-compatible, said at least one imaging modality comprises a magnetic resonance imaging system, and said control module calculates an estimated temperature at a selected position within said body using data drawn from analysis of both a first MRI image created prior to freezing of a portion of said body by said cryoprobe and a second MRI image created subsequent to freezing of a portion of said body by said cryoprobe.

49. A method for guiding guided cryosurgery by calculating an estimated border of a cryoablation volume within the body of a patient based on data provided by an imaging modality, comprising:
(a) recording a position of a cryoprobe within tissues of said body prior to creating an iceball surrounding said probe;
(b) cooling said probe to form an iceball surrounding said probe, and recording positions of three-dimensional borders of said iceball;

(c) selecting a distance ratio usable to determine status of subunits of tissue within said iceball;
(d) digitally subdividing tissue within said iceball into subunits;
(e) determining for each subunit whether it is within an ablation volume by calculating a first distance of said each subunit from a nearest cooling portion of said cryoprobe and a second distance of said each subunit from a nearest border of said iceball, and determining that said subunit is within said ablation volume if said first distance divided by a sum of said first and second distances is less than said selected distance ratio, and determining that said subunit is outside said ablation volume if said first distance divided by a sum of said first and second distances is greater than said selected distance ratio.

50. The method of claim 49, further comprising displaying an image of at least a portion of said estimated cryoablation volume border.

51. The method of claim 49, further comprising comparing said estimated cryoablation volume border to a predetermined cryoablation target to determine whether said predetermined cryoablation target is contained within said cryoablation volume.

52. The method of claim 51, further comprising issuing notification to a surgeon if said cryoablation target is determined to be contained within said cryoablation volume.

53. The method of claim 51, further comprising issuing a command to a cryoablation apparatus if said cryoablation target is determined to be contained within said cryoablation volume.

54. The method of claim 49, wherein said imaging modality comprises a magnetic resonance imaging system.

* * * * *